United States Patent [19]
Fuchs et al.

[11] Patent Number: 5,813,570
[45] Date of Patent: Sep. 29, 1998

[54] APPARATUS FOR CONTROLLABLY DISCHARGING FLOWABLE MEDIA

[75] Inventors: Karl-Heinz Fuchs; Stefan Ritsche, both of Radolfzell, Germany

[73] Assignee: Ing. Erich Pfeiffer GmbH, Germany

[21] Appl. No.: 594,055

[22] Filed: Jan. 30, 1996

Related U.S. Application Data

[63] Continuation-in-part of Ser. No. 571,942, Oct. 8, 1996, abandoned.

[30] Foreign Application Priority Data

Apr. 8, 1994 [DE] Germany ........................ 44 12 041.9
Feb. 9, 1995 [WO] WIPO ................. PCT/EP95/00457
Jan. 23, 1996 [DE] Germany ...................... 296 01 047 U

[51] Int. Cl.⁶ ............................................. B67D 5/00
[52] U.S. Cl. .................. 222/82; 222/83; 222/153.06; 604/203
[58] Field of Search .................... 604/203; 222/82, 222/83, 83.5, 309, 327, 153.06, 153.13

[56] References Cited

U.S. PATENT DOCUMENTS 3,403,823 10/1968 O'Donnell .
4,964,069 10/1990 Ely .
5,307,953 5/1994 Regan .
5,469,989 11/1995 Graf et al. .

FOREIGN PATENT DOCUMENTS 546607 6/1993 European Pat. Off. .
1535293 8/1968 France .

*Primary Examiner*—Gregory L. Huson
*Attorney, Agent, or Firm*—Quarles and Brady

[57] ABSTRACT

A discharge apparatus for flowable media, comprising: a basic body, at least partly receiving a pump unit; the pump unit having a pump chamber connectable to a discharge opening via a discharge channel; a pump cylinder and a pump piston bounding the pump chamber; the pump cylinder forming a medium reservoir; the pump piston being displaceably guided in the pump cylinder for discharging all the medium contained in the medium reservoir by a single pump stroke in a pump stroke direction; and, at least one breakable material bridge between the pump unit and the basic body which can be destroyed by an actuating force exerted in the pump stroke direction, whereby the medium is discharged from the apparatus with a predetermined discharging pressure by a predetermined actuating force level and the apparatus is provided with a destroyable tamper-evident closure.

24 Claims, 7 Drawing Sheets

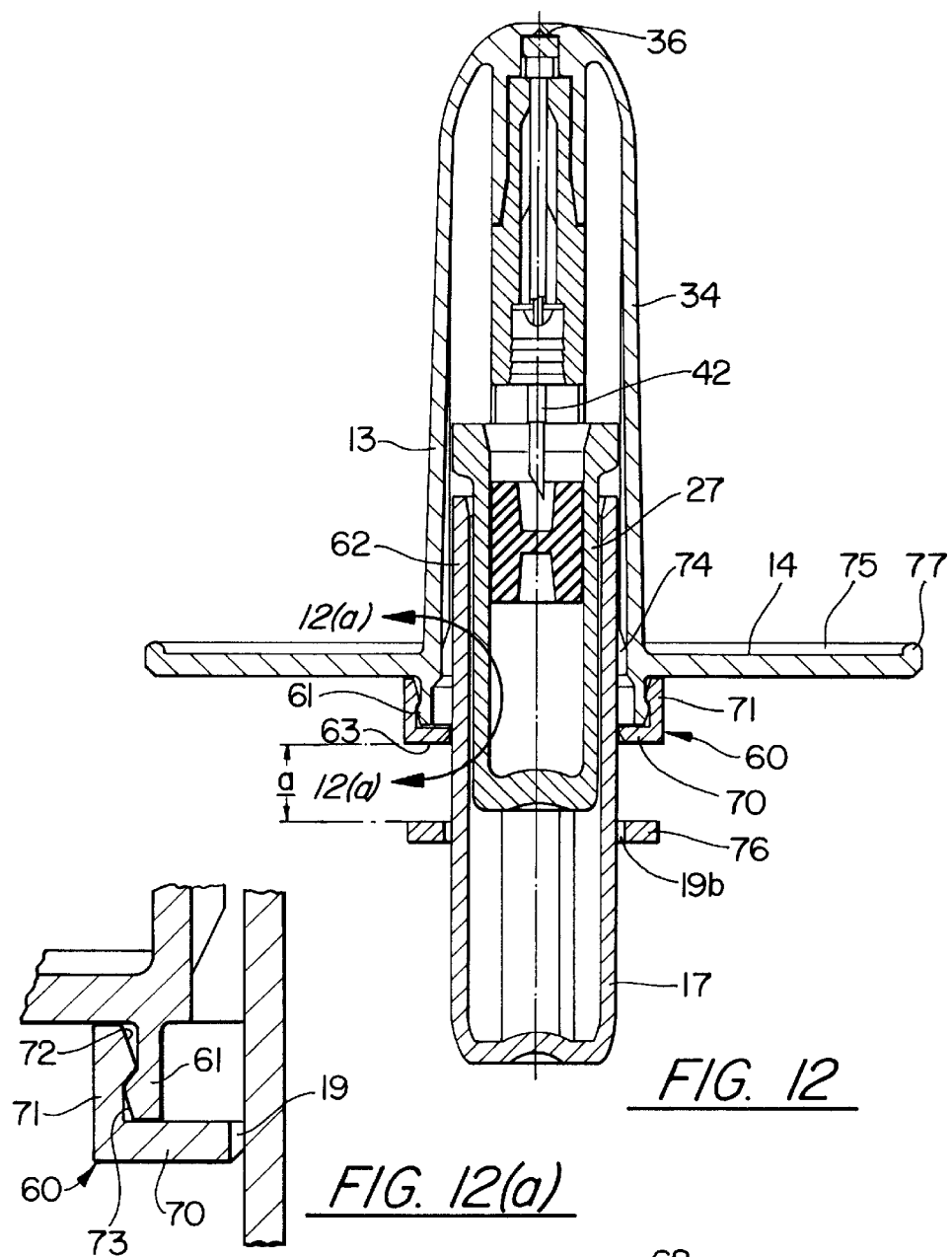
FIG. 12
FIG. 12(a)
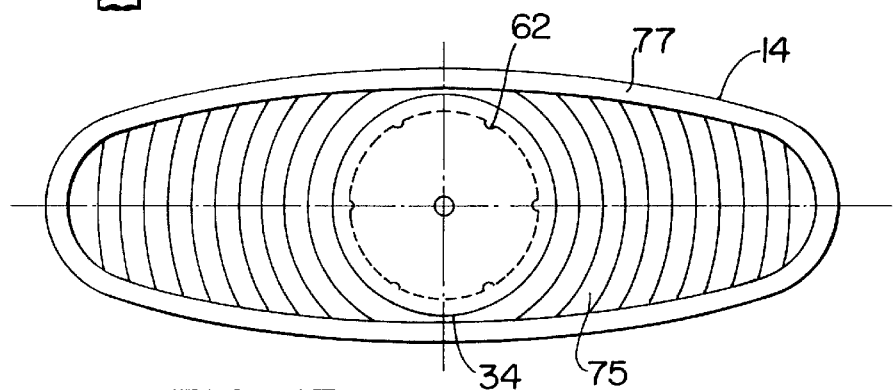
FIG. 13

APPARATUS FOR CONTROLLABLY DISCHARGING FLOWABLE MEDIA

This application is a continuation-in-part of application Ser. No. 08/571,942 filed Oct. 8, 1996, now abandoned.

BACKGROUND OF THE INVENTION

1. Field of the Invention

The invention relates to the field of discharge apparatus for flowable media, and in particular, to a single stroke discharge apparatus.

2. Description of Related Art

A discharge apparatus is described in EP 311 863, corresponding to U.S. Pat. No. 4,964,069 of the present applicant. The pump cylinder and a resilient stop constructed in the manner of a snap locking means cooperate in such a way that, prior to the discharge of a partial stroke, a specific actuating pressure must be applied by the operator, so that after overcoming this pressure point the discharge of the liquid takes place with a certain minimum force and speed.

This construction ensures that e.g. on atomizing the medium the pressure from the first instant is sufficient for atomization purposes and that the pump is actuated up to its end, i.e. performs the complete stroke and the entire content of its medium reservoir, which simultaneously forms the pump cylinder, is discharged in one or two strokes. Such single or double dosing or proportioning devices are advantageous for the dispensing of medicaments, which are particularly critical with respect to proportioning, contamination, preservation or other criteria.

WO 92/00812 of the applicant also discloses the use of medium reservoirs for a single discharge stroke, which are sealed by a plug simultaneously serving as the piston, the plug being perforated by a needle for actuation purposes. The medium reservoir is received in a sleeve, which has external projections and which cooperate with corresponding projections on the inside of a casing basic body in the manner of a snap fastening. On actuation it is firstly necessary to overcome the static friction, before said beads slide on the faces against which they engage, so that a pressure point must be overcome.

It is a problem in such a discharge apparatus to prevent an accidental double use or incomplete actuation, while avoiding the resulting contamination or proportioning problems.

SUMMARY OF THE INVENTION

The problem is solved by a tamper-evident closure which can be destroyed by an actuating force.

The tamper-evident closure can in an embodiment of the invention be formed by at least one material bridge between at least one pump portion movable with the pump cylinder and a casing portion connected to the basic body. The material bridge is advantageously formed by a one-piece construction of the casing and pump portions.

Therefore, a predetermined breaking point is created between the mutually movable parts of the discharge apparatus, the intact condition of which is a sure sign that the charge of filling of the medium reservoir is unopened and unused. The user can establish this e.g. optically or by a slight turning of the actuating part. To facilitate checking, window cutouts can be provided or parts of the pump can be made from transparent material. It is also possible to use a plastics material, which discolours in the case of a breaking deformation. Marks on the movable portion and the casing would also be possible. The material bridge is preferably formed between an actuating sleeve retaining, and optionally partly receiving, the pump cylinder serving as the medium reservoir and an inner portion of a base casing part provided with actuating shoulders. The actuating shoulders serve as a support for two fingers, the thumb pressing on the actuating sleeve. An adequate force can be applied in order to shear or tear off the material portion. As a result of the force applied, an adequate actuating force is simultaneously produced for a reliable actuation of the pump.

The material bridges can e.g. be provided on the outer circumference of the actuating sleeve and between the latter and a ring surrounding said sleeve, which is in turn fixed to the facing part, i.e. to the casing, by snapping in. This makes it possible to manufacture the actuating sleeve separately from the casing. However, the material bridges could also be shaped onto the casing and the circular fastening element could be fixed to the facing, movable part, the pump cylinder or the actuating sleeve, by engagement or in some other way.

It is especially advantageous if the element which is shaped onto the pump part via the material bridges, encloses a projection of the housing from the outside. In this case, the element covers the connecting gap between the pump part and the housing completely and provides not only an optical and functional merge between pump part and housing but also prevents every possibility of manipulation of the tamper-evident connection. It should be preferably provided that the snap-in connection is secured against drawing off, such that it is destroyed if someone tries to draw off the pump cylinder from the housing. In this case, the material bridges and the tamper-evident closure shall break.

It is especially preferred that the element is a ring with an L-shaped cross section consisting of a substantially radial bottom ring part and an adjacent jacket. The inside of the jacket is preferably provided with a snap profile. This snap profile can cooperate with a correspondingly shaped profile at the ring or ring segment shaped projection in snap acting manner.

So as to be able to insert in the discharge apparatus the pump cylinder, which contains the medium and which is normally made from glass so as to prevent diffusion and for compatibility reasons, preferably the base casing part is connected to a connector portion at least partly receiving the pump and having the discharge opening, e.g. by locking engagement.

Advantageously several material bridges are uniformly distributed over the circumference of the interconnected parts in order to prevent tilting during actuation. These material bridges can advantageously be located in an area, in which one of the parts, e.g. the actuating sleeve, has its terminal edge, while the other actuating part starts above and somewhat outside the same. It forms there a separating plane between mutually cooperating mold parts in the plastic injection molding process, between which the material bridges are left behind in the manner of a flash, but with a controlled predetermined breaking force.

In order to permit a reliable separation of the material bridges with a predetermined force, on one of the parts cooperating during the actuation of the pump and preferably on the basic body could be provided a cutting edge for the cutting through of the material bridge. It can e.g. be an inner edge of the connector portion connected to the base casing part. Whereas without such a cutting edge it is advantageous to mainly apply a shear stress greater than this predetermined breaking point. In this case, which is also advantageous when using materials with a high breaking elongation, a web-like shaping of the material bridges is also appropriate.

According to another embodiment the tamper-evident closure in the vicinity of a ram piercing the piston plug forming the pump piston can be formed by a ram design producing increased resistance prior to piercing. Thus, deliberately, a controlled resistance opposes the ram before it initiates the start of the pump stroke on piercing. Unlike in the case of a needle construction, which mainly aims at piercing the piston plug with the minimum possible force, here a resistance is accepted in planned manner. However, it must be ensured that the piercing takes place without any detachment of parts from the piston plug, so that such parts cannot enter the medium and clog the discharge nozzle.

The ram can e.g. be made from plastic and namely together with an otherwise active pump part, which e.g. avoids the extra expenditure which would result from the introduction of a steel needle. Although in the case of the relatively large dimensions, which the ram can have due to its function, the construction of an inner channel therein would not be particularly problematical. It is much easier from the manufacturing standpoint if the ram has lateral conduits for the medium, in which it e.g. has a cruciform cross-section. The conduits, which then pass the medium through the piston plug, are then sealed from the outside by the plug. It is advantageous if the bottom of the piston plug, which is pierced, is located at the end of a depression, which surrounds the ram and therefore bounds the conduits. An upper face of the piston plug can cooperate with a corresponding part on the pump, so as to also there create a seal to the outside.

When the ram penetrates this depression the necessary counterpressure can be produced as is needed for the tamper-evident closure, and by means of the previously described markings or other measures, it is possible to read off whether or not the pump has already been actuated.

These and further features can be gathered from the claims, description and drawings. The individual features, both singly and in the form of subcombinations, can be implemented in an embodiment of the invention and in other fields and can represent advantageous, independently protectable constructions.

BRIEF DESCRIPTION OF THE DRAWINGS

FIG. 12 is a longitudinal section through a further preferred embodiment.

FIG. 13 is a top view of the embodiment of FIG. 12.

DETAILED DESCRIPTION OF THE PREFERRED EMBODIMENTS

Figure 1:
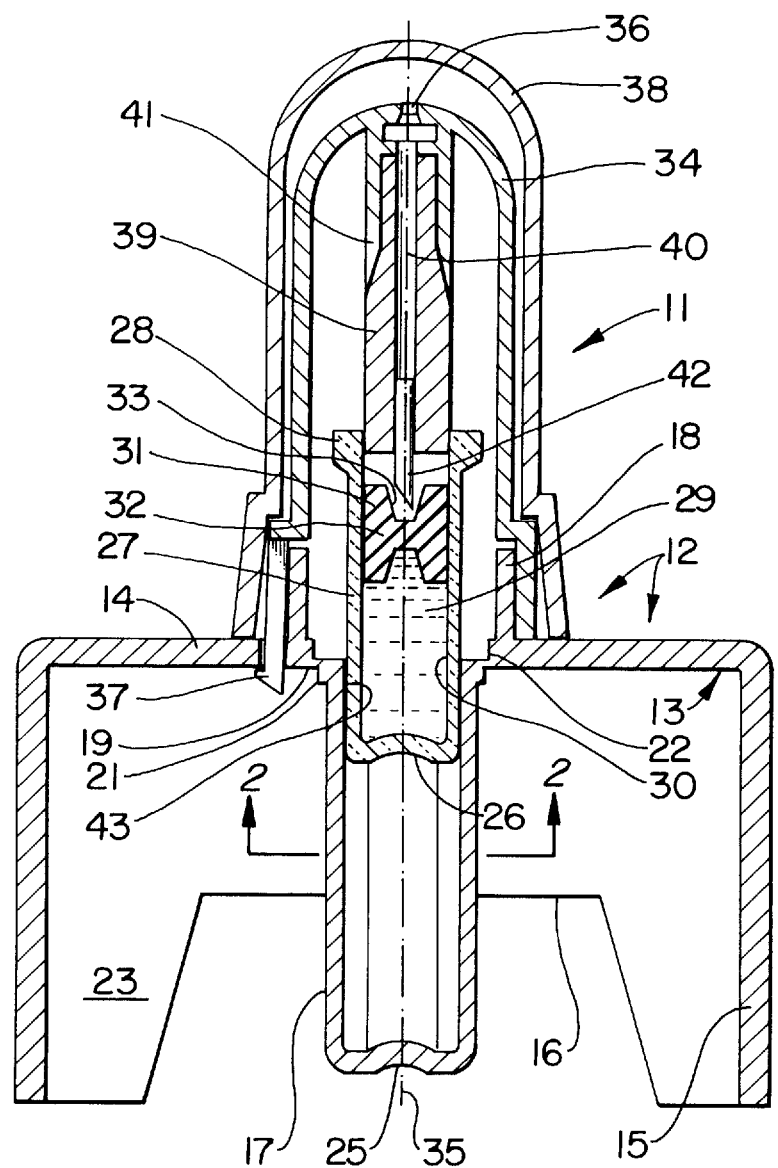
FIG. 1 is a longitudinal section through a discharge apparatus with a tamper-evident closure.

The discharge apparatus 11 shown in FIG. 1 has a two-part basic body 12. It contains a base casing part 13, which has an epaulette-like shape with two actuating shoulders 14 and a jacket 15 connected thereto. The base casing part is flat or flat-oval and has its greatest extension in the drawing plane, whereas it has smaller dimensions transversely thereto. The jacket 15 is longer on the right and left-hand sides in FIG. 1 and has on its two sides roughly parallel to the drawing plane a cutout 16, which is open to the bottom.

Figure 2:
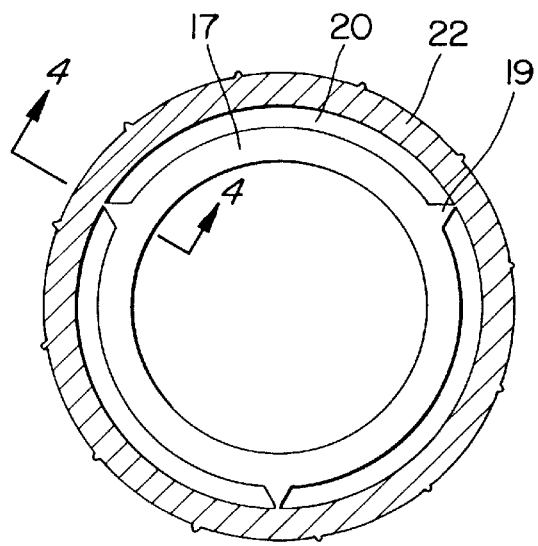
FIG. 2 is a view in the direction of the arrow II in FIG. 1.
Figure 3:
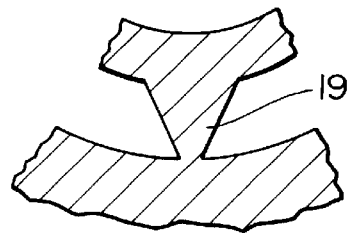
FIG. 3 is a detail from FIG. 2, but shown in section.
Figure 4:
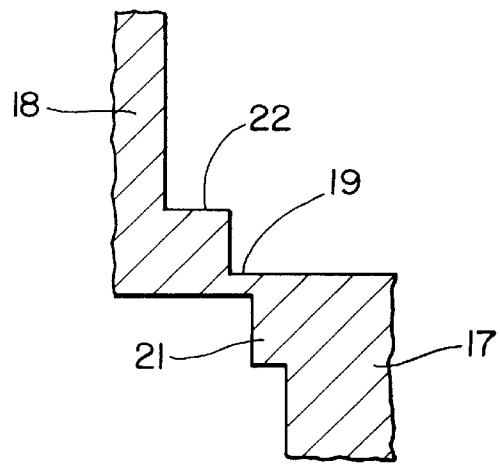
FIG. 4 is a section along line IV in FIG. 2.

On the base casing part 13 is injection molded in one piece an actuating sleeve 17, namely on the lower, inside of a connector 18 projecting upwards from the part 13. The one-piece connection between the base casing part 13 and the actuating sleeve 17 takes place by means of material bridges 19, as shown in FIGS. 2 to 4. The gap 20 between the outer edge of an upper flange 21 of the actuating sleeve and an inner flange projection 22 in the interior of the connector 18 is bridged in the represented embodiment by three thin connecting webs, which have a triangular shape and whose tip is shaped on the web 22, so as to form predetermined breaking points. From the manufacturing standpoint, as a result of correspondingly small recesses, which scarcely exceed the dimensions of a normal flash, they can be formed on the separating face between two plastic injection molded parts, which on the one hand form the space 23 in the interior of the jacket 15 and on the other the space in the connector 18. Correspondingly the three uniformly, circumferentially distributed material bridges 19 are located in a plane formed by the inside and bottom of the actuating shoulders 14 on the one hand and the upper edge of the flange 21 on the other.

The actuating sleeve 17 has inner ribs 24, which roughly take up ¾ of the length of the sleeve, considered from its bottom 25. On the same is supported the bottom 26 of a pump cylinder 27, which has the shape of a roughly cylindrical, bottom closed sleeve made from glass and having an upper side flange 28. It simultaneously forms the reservoir for the medium 29 to be discharged and the pump cylinder. Its inner circumferential surface consequently forms the piston runway or cylinder, 30 for a piston 31, which is constructed in the form of a rubber or similar elastic material piston plug. In longitudinal section it has a H-shape and is a thick-walled tube, whose outer jacket forms the piston runways, with a central closure web 32 transversely closing the tube interior, so that at the top and bottom, connecting onto the closure web 32 depressions 33 are formed, which can be roughly conical.

The piston plug 31 is located on the hermetically sealed medium 29. Filling takes place with or without air inclusions. The pump cylinder is inserted with slight pressure in the upper part of the actuating sleeve and extends with its largest part over and beyond the actuating shoulders 14 through the connector 18 and into a connector portion 34, which can also be constructed as an adaptor. It is a finger-like portion, which has a substantially cylindrical or slightly conical shaft with an upper, spherical round portion running in the direction of the pump axis 35. In the center of the round portion is provided the discharge opening 36 in the form of a conventional spray nozzle. However, the discharge opening could also be provided for some other discharge form, e.g. for a dosed delivery of a liquid or pasty medium. The discharge opening could have other shapes, so as to permit better adaptation of the delivery to the shape of any body opening. Therefore it is also advantageous to manufacture the connector portion 34 separately from the base casing part and to fix the connector portion thereto by a snap fastening 37 with e.g. three tabs engaging in openings and provided with a barb-like head, the connector portion being centered on the connector 18. In order to prevent a removal of the connector portion 34, the snap fastening can be constructed in self-locking manner. A protective sleeve 38 protects the connector portion against contamination.

In the interior of the connector portion there is a piston rod portion 39, which has an inner discharge channel 40 and is inserted in the sleeve 41 shaped inwards on the upper end of the connector portion 34. In the piston rod portion 39 is inserted a ram 42 in the form of a downwardly inclined cut-off, hollow steel needle, e.g. by injecting or pressing into an opening provided with corresponding retaining ribs.

Except for the steel needle 42, the piston plug 31 made from rubbery materials and the glass pump cylinder/medium reservoir, all pump parts are plastic injection moldings.

During manufacture in the component surrounding the base casing part 13 and the actuating sleeve 17 the pump cylinder 27 is inserted from above in the receptacle 43 formed in the actuating sleeve 17. The cylinder 27 contains the medium 29 tightly sealed through the piston plug 31.

This is followed by the mounting of the connector portion, on which have been preassembled the piston rod portion and the ram 42. The connector portion engages in the base casing part and is fixed via the snap fastening 37. Thus, after fitting the protective sleeve 38, the discharge apparatus is assembled. For use purposes, following the removal by the user of the protective sleeve 38, the discharge apparatus is taken up between three fingers, two fingers resting on the shoulders 14 and the thumb on the bottom 25 of the actuating sleeve 17. The thumb engages in the window-like cutout 16 and consequently has an adequate actuating clearance. The discharge opening 36 is directed onto the corresponding point and by a powerful pressure on the actuating sleeve the actuating pressure is built up to such an extent that the predetermined breaking points formed by the material bridges 9 tear or shear and the actuating sleeve can be moved upwards together with the pump cylinder. As a result of the prior, powerful pressure build-up this takes place with a high speed, which ensures a speedy performance of the discharge stroke taking place. The pump cylinder is moved upwards against the ram 42, so that the latter pierces the central web 32 of the piston plug, but as a result of the elasticity of the piston plug material, is immediately resealed on the outer face. Only through the inner channel of the ram constructed as a hollow needle, can the medium escape upwards through the discharge channel 40 and the discharge opening 36, and be delivered there, in sprayed or correspondingly proportioned manner. The lower edge of the piston rod portion 39 can engage on the upper face of the piston plug 31 and consequently produce a direct pressure connection with the piston, which runs downwards along the piston runway 30 and conveys the medium to the discharge opening. The length of the needle should be such that it does not project over the lower boundary of the piston plug 31, so that an almost complete discharge of the medium, which in certain circumstances is very expensive, is ensured.

Thus, the discharge apparatus offers a possibility of discharging sensitive and expensive materials in a planned and precisely dosed manner. Through the tamper-evident closure operating with material destruction it is possible at any time to check the intact condition and it is ensured that there is a complete delivery of the medium with an adequate actuating pressure. The apparatus is simple to manufacture and fit, and can easily be adapted to different circumstances, e.g. by different adaptor shapes. Following actuation, the unit comprising the pump cylinder 27 and actuating sleeve is loose and can optionally be drawn out in the downwards direction. The pump cylinder 27 with the pump plug 31 can be removed, so that the remainder, with the exception of the small needle, is made from one type of material, optionally plastic and can be correspondingly disposed of.

Figure 5:
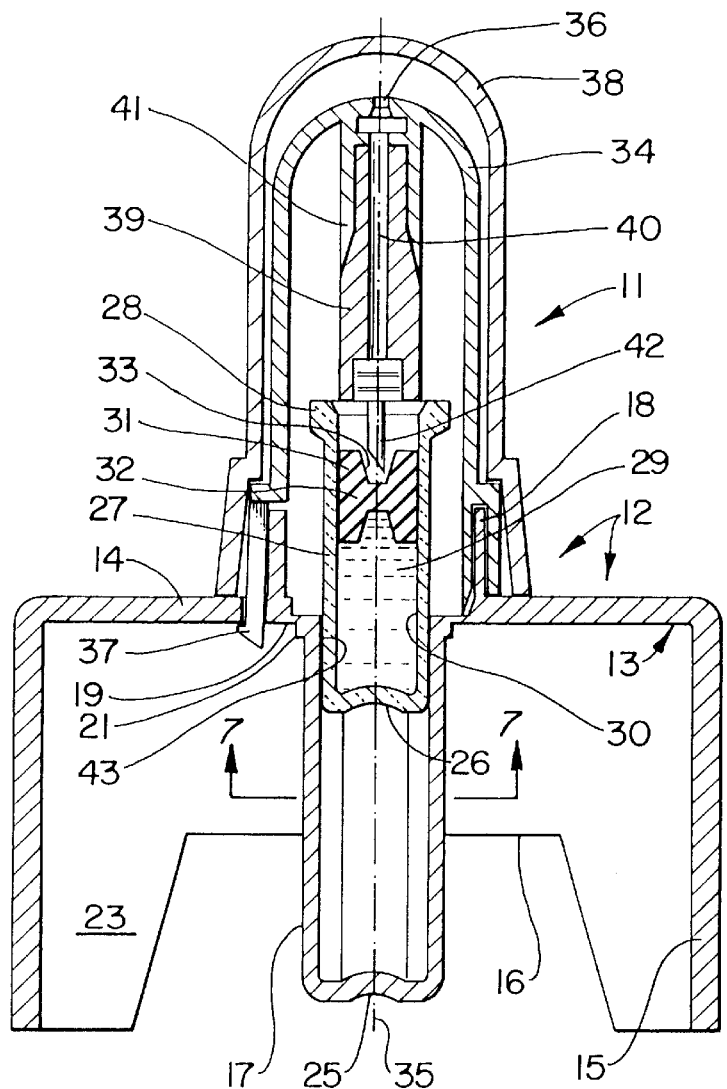
FIG. 5 is a modified embodiment of the discharge apparatus according to FIG. 1 in longitudinal section.

In the embodiment according to FIG. 5 all parts and functions are identical with those of FIGS. 1 to 4, apart from the following exceptions.

Figure 7:
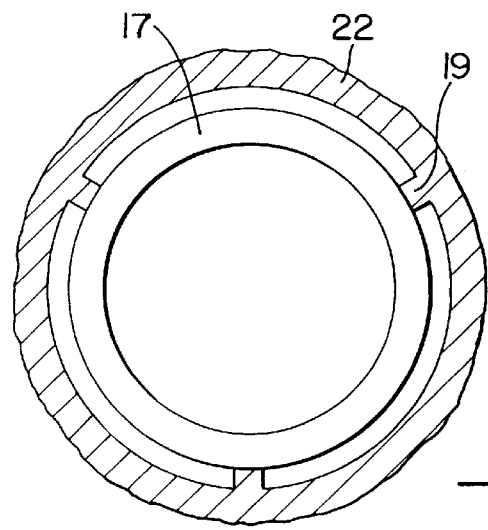
FIG. 7 is a view in the direction of arrow VII in FIG. 5.

As shown in FIG. 7, the material bridges 19 are constructed as strip-shaped webs and consequently have no such marked, almost punctiform predetermined breaking point as in the case of the triangular material bridges of FIGS. 2 and 3. However, in order to ensure a clean and precise separation, a cutting edge 55 is provided, which in the represented embodiment is shaped onto a lower inner edge of the connector portion 34. The latter engages in the manner of a circular pocket over the connector 18 of the base casing part 13.

Prior to operation the cutting edge 55 rests on the material bridge or projects somewhat over it. On actuation the material bridge is pressed against the cutting edge 55 and cut off, which is particularly advantageous if the material has a considerable breaking elongation. This cutting edge construction could also be provided on other pump components and used with other material bridge shapes. When reference is made hereinbefore to three circumferential material bridges, this merely represents an advantageous construction permitting a tilt-free actuation, without there having to be an excessive number of material bridges, but a different number could also be chosen.

Figure 8:
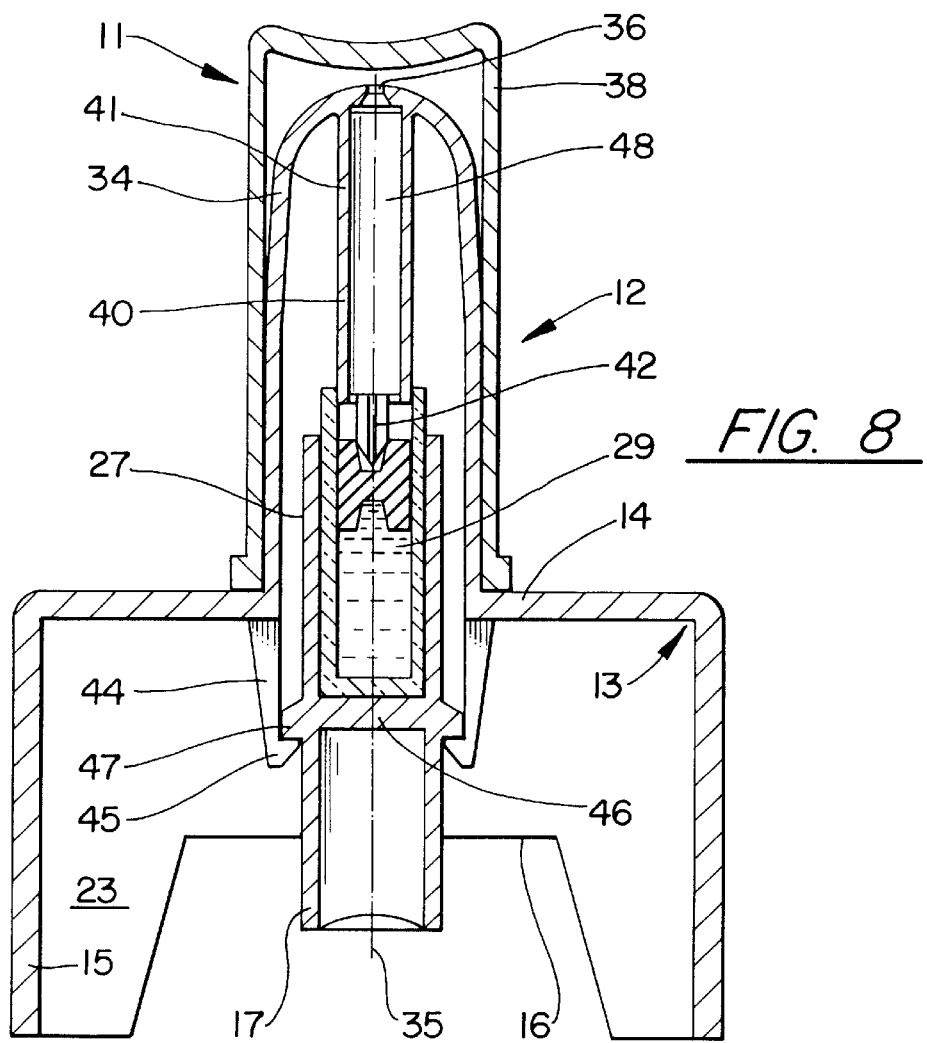
FIG. 8 is a longitudinal section through another embodiment of the discharge apparatus.

FIG. 8 shows an embodiment which, with respect to the shaping of the basic body 12, is largely the same as those described hereinbefore. However, in this case the basic body 12 with the base casing part 13 and the connector portion 34 are made from a plastics part. At the bottom, i.e. into the space 34 retaining clips 44, whose ends have barb-like latching projections, are connected to the connector portion 34.

In place of the lower bottom 25, the actuating sleeve 17 has an intermediate bottom 46, which bounds the receptacle 43 for the pump cylinder 27 and an outer guide flange 47, which engages on the substantially axially directed inside of the retaining clips 44, which run in the extension of the inner faces of the connector portion 34.

Figure 10:
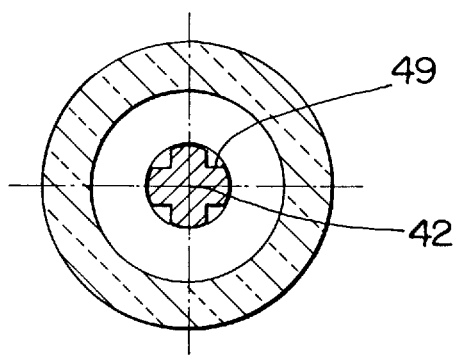
FIG. 10 is a cross-section along line X in FIG. 9.

The spray nozzle forming the discharge opening is formed between the latter and the piston rod insert 48, which is located in a sleeve 41 extending up to the pump cylinder and which is shaped in the interior of the connector portion 34. The piston rod insert 48 is pressed in there and has a lateral discharge channel 40 in the form of a groove, and on its upper end face corresponding spiral groove constructions, which belong to the vortex die. Onto the underside of the piston rod insert is shaped the ram 42 which, like the latter, is made from plastic. It is downwardly tapered or provided with a cutting edge and has a cruciform cross-section as can be seen in FIG. 10. Between the cross ribs are formed channels 49.

Figure 9:
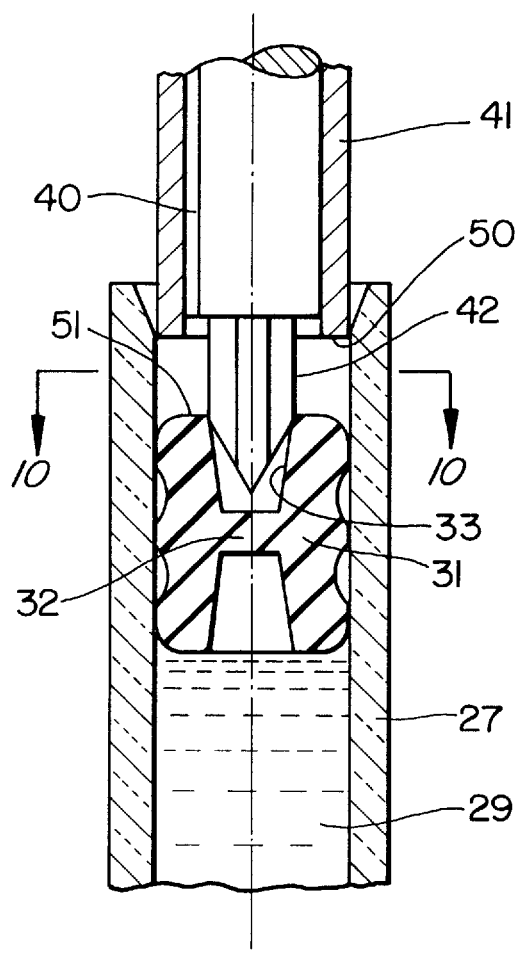
FIG. 9 is a detail of FIG. 8.

As can in particular be gathered from FIG. 9, the external dimensions of the ram are so large that it must be pressed into the depression 33 on the piston plug 31.

Figure 6:
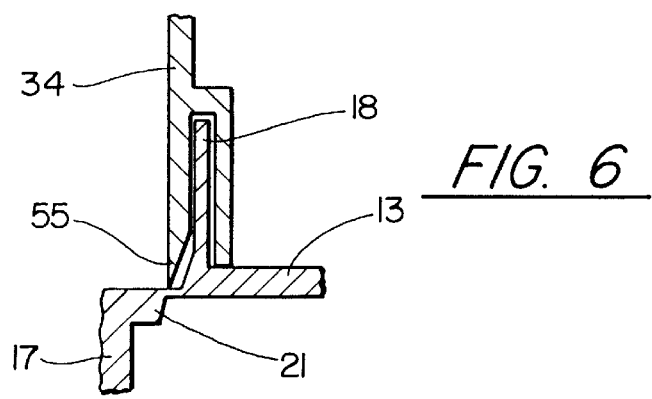
FIG. 6 is a detail from FIG. 5.

All the remaining parts are the same as in the previous embodiments and are given the same reference numerals in FIGS. 5 to 7 as in FIGS. 1 to 4.

In this embodiment assembly can take place by plugging together two preassembled units, namely on the one hand the basic body 12 in which has been pressed the piston rod insert 48, and on the other the unit comprising the actuating sleeve 17 and the filled and sealed pump cylinder 27 inserted therein. Insertion can take place from the bottom in the axial direction until the guide flange 47 engages behind the latching projections 45.

During actuation pressure is exerted on the lower end of the actuating sleeve 17. As in WO 92/00812, the forces resulting from the static friction between the engaging parts 44, 47 must be overcome and the ram 42, accompanied by the deformation of the piston plug must be forced into the latter until the closure web 32 is pierced. This requires a relatively high actuating force, which is deliberately chosen higher than would normally be necessary for piercing the web 32. Under the pressure of the ram, the piston plug cannot be pressed further into the pump cylinder, because the medium is normally incompressible. Only after the piercing of the closure web can it pass out upwards through the channels 49. The latter have in the meantime been sealed to the outside by the inner wall of the depressions 33 and by the engaging of the lower face 50 of the sleeve 41 on the upper edge 51 of the closure plug 31, so that the medium is passed through the discharge channel 40 to the discharge opening 36.

Figure 11:
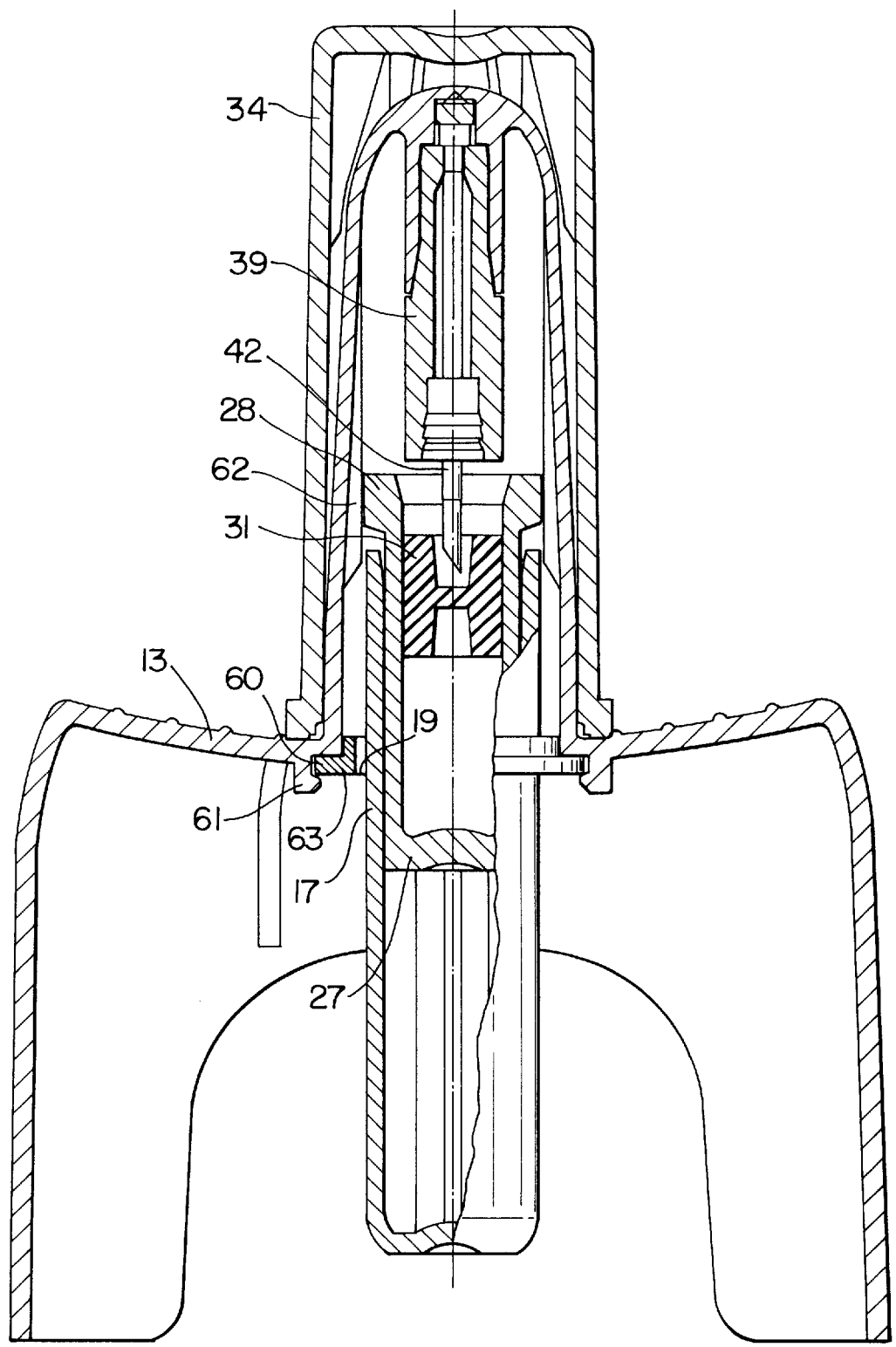
FIG. 11 is a partial longitudinal section through an embodiment with a shaped on tamper-evident closure ring.

FIG. 11 shows in longitudinal section a detail of an embodiment, in which the casing 13 and connector portion 34, as in FIG. 8, are constructed in one piece. Otherwise the construction is similar to FIGS. 1 and 5. The same reference numerals are used for the same parts and reference is made to the previous description of the parts and their function.

On the actuating sleeve 17, which receives the container 27, is provided on the outside a fastening element 60 in the form of an all-round ring with an L-shaped cross-section. It is connected to the actuating sleeve 17 by several material bridges 19, which are so constructed and dimensioned, that they tear away under the actuating pressure and consequently separate the ring from the actuating sleeve. The fastening element 60, actuating sleeve 17 and material bridges 19 are injection molded from plastic in one piece.

The fastening element 60 is fixed to the casing 13 by a snap connection 61. The fastening element is centered with its axial leg on the inside of the connector portion 35, whereas the outwardly directed leg latches in a depression at the transition between the actuating shoulder 14 and the connector portion 34.

During assembly the actuating sleeve is introduced together with the container 27 forming the pump cylinder. An assembly tool can press the lower engagement face 63 of the actuating element 60 in FIG. 11, so that engagement of the latching connection 61 takes place without any risk of damage to the tamper-evident closure formed by the material bridges 19. However, if the user moves the sleeve upwards, the material bridges 19 tear and the actuating sleeve, together with the pump cylinder/container 27, can perform the pump stroke in the previously described manner. The actuating sleeve 17 is guided on the one hand in the circular fastening element 60 (between the torn off material bridges) and on the other on the inner webs 62 of the connector portion 34. An outer flange of the container/pump cylinder 27 is also guided in this way, which prevents tilting of the actuating means. The material bridges 19 can also be constructed as split or through film connections.

The fastening element 60 has a certain amount of axial and radial clearance in the latching connection 61. This makes it possible to intentionally or unintentionally turn the actuating sleeve 17 without destroying the tamper-evident closure. However, the latching connection must be sufficiently strong that on drawing off the actuating sleeve 17 in the downwards direction the tamper-evident closure tears. This ensures that there have been no undesired manipulation of the content, of the proportioning device.

Thus, a tamper-evident closure has been provided, which requires a higher, material-destroying actuating force in order to unseal the medium reservoir 27, than would be needed in the case of a simple needle. This is aided by the frictional force between the guide flange 47 and the retaining clips 44 which, after overcoming the static friction, pass into the sliding state and therefore release a larger proportion of the expended actuating force for actuation and overcoming the other resistances.

FIGS. 12 and 13 show a preferred embodiment which has the same structural and functional features as the embodiment of FIG. 11. Here also the same reference numerals are used for the same parts and reference is made to previous description of those parts and their function.

The element 60 which is connected to the actuating sleeve 17 by the material bridges 19, is a ring with an L-shaped cross section. Accordingly it has a bottom ring 70 which has at its inner side the material bridges 19 connecting the bottom ring 70 integrally with the actuating sleeve 17. Parallel and concentric with the actuating sleeve 17 is a jacket 71. At the inner surface of the jacket 71 there is provided a snap profile 72 which can e.g. consist of a barbed ring projection (see the enlarged detail in the dash-dotted circle in FIG. 12)

The element 60 covers a housing projection 61, which is ring-shaped and surrounds the middle housing opening 74, in which the pump cylinder 27 and its actuating sleeve 17 is contained. The projection 61 projects over the housing 13 to below. The projection 61 can have a ring or tubular shape or be in the shape of several segments arranged in ring-shaped manner. At its outside it has a counter profile 63 matching to the snap profile 72 of the jacket.

Its snap action is provided such that during mounting of the unit actuating sleeve/pump cylinder 17, 27 in the housing opening 74, the element 60 is fixed by snap action at the housing projection 61 and covers the latter. The power needed for snapping-on is such that during snapping-on the material bridges will not be over-stressed. If, however, a power in the counter direction is exerted which could lead to a withdrawal of the actuating sleeve 17 to below, the barbed shape of the snap means 72, 73 provide that the material bridges 19 will be destroyed, thereby clearly evidencing tampering.

While in the embodiment of FIG. 11 the housing has a housing jacket 15 projecting to below, the embodiment of FIGS. 12 and 13 provides actuating shoulders 14 having the shape of flat housing projections (FIG. 13) projecting laterally far past the main portion 34 of the housing in two opposite directions. It has a generally oval shape. It enables a safe grip of the apparatus between two fingers when pressing the thumb on the lower bottom 25 of the actuating sleeve. Ribs 65 which are to be seen from FIG. 13 provide good grip and stiffening, especially by a peripheral edge rib 77 projecting to above.

Material will thereby be saved without impairing stability, which is of great importance for a single use product. Further the lower surface of the actuating shoulder 14 can be used for attaching markings, for instance batch numbers. The actuating sleeve 17 can also be used for labels or other visual marks.

At the outer circumference of the actuating sleeve 17 there is provided a second ring-shaped element 76 at the distance a from the lower surface 63 of element 70. Like element 70, the second element 76 is also molded in one piece with the actuating sleeve via material bridges 19b which may be of the kind as shown in FIGS. 2 to 4. They may however be somewhat stronger than those of element 60.

This embodiment provides a double stroke discharge device, i.e. a discharge or spray device which is able to discharge two exactly proportioned charges in succession. The ring-shaped element 76 terminates the operation after the first part of the stroke, equivalent to the distance a. At this end of this part of the stroke the operation force (counter pressure of the liquid etc.) and the force for breaking the material bridges 19 are adding up. It is therefore unlikely that the user can overrun the second ring unintentionally.

After this stop, which is usually half the way of the complete stroke, the user can also break the material bridges 19b by an increased pressure on the pump part. When breaking the material bridges 19b, the ring-shaped element 76 abuts the contact surface 63 of element 60.

After the first part of the stroke of this two stroke discharge apparatus, the container or pump cylinder 26 is open via the hollow needle 36. For the use of a nasal spray, this embodiment is however very advantageous for applying a medicine into both nostrils consecutively but in even proportion. The second stroke is thereby also tamper-proof.

It is to be noted that the embodiment of FIG. 12 provides a closed and uncomplicated discharge apparatus which is easy to operate and to pack.

What is claimed is:

1. Discharge apparatus for flowable media, comprising:
    a basic body, at least partly receiving a pump unit;
    said pump unit having a pump chamber connectable to a discharge opening via a discharge channel;
    a pump cylinder and a pump piston bounding said pump chamber;
    said pump cylinder forming a medium reservoir;
    said pump piston being displaceably guided in said pump cylinder for discharging all said medium contained in said medium reservoir by a single pump stroke in a pump stroke direction; and,
    at least one breakable material bridge between said pump unit and said basic body which can be destroyed by an actuating force exerted in said pump stroke direction, whereby said medium is discharged from said apparatus with a predetermined discharging pressure by a predetermined actuating force level and said apparatus is provided with a destroyable tamper-evident closure.

2. Discharge apparatus according to claim 1, wherein the at least one material bridge is formed by a one-piece construction of the casing and pump portions.

3. Discharge apparatus according to claim 1, wherein a ring shaped fastening element is via the at least one material bridge integral with one portion of a group of portions including a casing portion and a pump portion; said fastening element being fitted to the other portion of said group of portions.

4. Discharge apparatus according to claim 3, wherein the fastening element surrounds an outer projection of the housing, the cooperating snapping means being provided at the outside of the projection and on the inside of the fastening element.

5. Discharge apparatus according to claim 4, wherein the fastening element is a ring with L-shaped cross section consisting of a bottom ring portion and a substantially cylindrical jacket portion.

6. Discharge apparatus according to claim 5, further comprising at the inner side of the jacket portion a snap profile cooperating with a correspondingly shaped snap profile at the outside of the projection.

7. Discharge apparatus according to claim 3, wherein the snapping means are barb-like to provide a smaller holding force in snapping-in direction than in a direction opposite thereto, in which opposite direction the holding force being greater than a force to break the at least one material bridge.

8. Discharge apparatus according to claim 5, wherein a guide for the pump portion being formed by the fastening element and inner webs of the basic body.

9. Discharge apparatus according to claim 3, wherein the fastening element has an engagement face for an assembly tool, exerting a force for engaging the snapping means.

10. Discharge apparatus according to claim 1, wherein the at least one material bridge is constructed in the interior of a base casing part provided with actuating shoulders which base casing part is locked to a central portion at least partly receiving the pump and including the discharge opening.

11. Discharge apparatus according to claim 1, wherein the at least one material bridge is formed integral with an actuating sleeve receiving at least partly the pump cylinder.

12. Discharge apparatus according to claim 1, further comprising several material bridges substantially in one plane.

13. Discharge apparatus according to claim 1, wherein the at least one material bridge is constructed in the shape of a tip connected to a wall.

14. Discharge apparatus according to claim 1, wherein the material bridge is constructed in the vicinity of an upper edge of an actuating sleeve and a downwardly directed edge in the interior of the casing portion.

15. Discharge apparatus according to claim 1, further comprising a cutting edge for cutting through the at least one material bridge.

16. Discharge apparatus for flowable media, comprising:
    a basic body at least partly receiving a pump chamber connectable to a discharge opening via a discharge channel, the pump chamber being bounded by a pump cylinder and a pump piston plug;
    said pump cylinder forming a medium reservoir;
    said pump piston plug being displaceably guided in said pump cylinder for discharging all said medium contained in said medium reservoir in a single pump stroke in a pump stroke direction;
    a ram arranged to pierce said pump piston plug under action of a predetermined axial actuating force applied to said piston plug in said pump stroke direction; and,
    said piston plug having a piercing resistance to the action of said actuating force,
    whereby said apparatus requires a predetermined actuating force level, and in response to said predetermined force level, discharges the medium with a predetermined discharge pressure and whereby said apparatus is provided with a destroyable, tamper-evident closure.

17. Discharge apparatus according to claim 16, wherein the ram has lateral channels for conducting the medium.

18. Discharge apparatus according to claim 16, wherein the ram is made from plastic and designed to penetrate, prior to piercing of a closure web in the piston plug, with its outer face sealingly a depression in the piston plug; a shoulder connected to the ram resting in sealing manner on a face of the piston plug.

19. Discharge apparatus according to claim 16, wherein the ram has at its tip a double-sided wedge shape.

20. Discharge apparatus according to claim 1, wherein on the pump unit a marking is provided cooperating with a marking on the basic body and which are mutually displaced during pump actuation.

21. Discharge apparatus according to claim 1, wherein between a tamper-evident closure position in which the parts movable against one another for actuation are fixed by said closure, and a discharge start position determined by the start of medium discharge, there is a spacing defining an idle path.

22. Discharge apparatus for flowable media, comprising:
a basic body at least partly receiving a pump unit;
said pump unit having a pump chamber connectable to a discharge opening via a discharge channel;
a pump cylinder and a pump piston bounding said pump chamber;
said pump cylinder forming a medium reservoir;
said pump piston being displaceably guided in said pump cylinder for discharging all said medium contained in said medium reservoir in two partial pump strokes;
a first and a second bridge element each having at least one breakable material bridge between said pump unit and said basic body which can be destroyed by an actuating force exerted in a pump stroke direction;
thereby providing both a predetermined actuating force level for discharging said medium with a predetermined discharging pressure during each of said partial pump strokes and destroyable tamper-evident closures for each of the partial pump strokes;
said first and second bridge elements being spaced such that said first bridge element allows, after breakage of its material bridges, said first partial stroke of said pump piston, said first partial stroke being limited by said second bridge element; and,
said pump piston being free for said second partial stroke after breakage of said material bridges of said second bridge element under a new predetermined actuating force, the pump piston is free for a second partial stroke.

23. Discharge apparatus according to claim 22, wherein the first element has an abutting surface on which the second element abuts at the end of the first partial stroke.

24. Discharge apparatus for flowable media, comprising:
a basic body at least partly receiving a pump unit;
said pump unit having a pump chamber connectable to a discharge opening via a discharge channel;
a pump cylinder and a pump piston bounding said pump chamber;
said pump cylinder forming a medium reservoir and being at least partly contained in a plastic actuating sleeve;
said pump piston being displaceably guided in said pump cylinder for discharging all said medium contained in said medium reservoir in at least one pump stroke;
said basic body having a central, substantially cylindrical portion having at its upper ends a spray nozzle and at its lower end actuating and gripping shoulders including a generally flat radial projection of considerably greater dimensions in two directions opposite to each other than in a direction perpendicular thereto;
at least one breakable material bridge integral with a fastening element and said actuating sleeve said material bridge being destroyable by an actuating force exerted in a pump stroke direction;
thereby providing both a predetermined actuating force level for discharging said medium with a predetermined discharging pressure and a destroyable tamper-evident closure;
said fastening element being a ring surrounding an outside housing projection;
said housing projection projecting from the underside of said gripping shoulders; and,
said actuating sleeve projecting centrally through and far beyond said fastening element.

* * * * *